United States Patent [19] [11] 3,980,716
Elliott [45] Sept. 14, 1976

[54] PRODUCTION OF ORTHO-PHENYLPHENOL FROM CYCLOHEXANONE

[75] Inventor: Christopher Stuart Elliott, Stockton-on-Tees, England

[73] Assignee: Imperial Chemical Industries Limited, London, England

[22] Filed: Apr. 2, 1973

[21] Appl. No.: 346,857

Related U.S. Application Data

[63] Continuation-in-part of Ser. No. 805,028, March 6, 1969, abandoned.

[30] Foreign Application Priority Data

Oct. 28, 1968 United Kingdom............... 51086/68
Mar. 15, 1968 United Kingdom............... 12646/68

[52] U.S. Cl.............................. 260/620; 260/586 C
[51] Int. Cl.²................... C07C 45/00; C07C 37/06
[58] Field of Search............ 260/621 H, 620, 586 R

[56] References Cited
UNITED STATES PATENTS

| | | | |
|---|---|---|---|
| 1,862,000 | 6/1932 | Britton et al........................ | 260/620 |
| 2,503,641 | 4/1950 | Taylor et al. .................... | 260/621 H |
| 2,719,863 | 10/1955 | Haslan ........................... | 260/586 C |
| 3,248,428 | 4/1966 | Porter et al...................... | 260/586 R |
| 3,397,239 | 8/1968 | Kelly............................... | 260/586 R |
| 3,542,878 | 11/1970 | Swift................................ | 260/586 C |
| 3,580,970 | 5/1971 | Swift................................ | 260/620 |
| 3,679,766 | 7/1972 | Kippax et al................... | 260/586 C |
| 3,746,733 | 7/1973 | Stapfer et al.................... | 260/586 C |
| 3,880,930 | 4/1975 | Ramm et al..................... | 260/586 C |

FOREIGN PATENTS OR APPLICATIONS

740,425 10/1943 Germany........................ 260/586 R

OTHER PUBLICATIONS

Plesek, "Coll. Czech. Chem. Commun." vol. 21, pp. 375–381, (1955)
Munk et al. "Chem. Abstracts" vol. 51, p. 11261 (1957).
Scheidt, "Chem. Abstracts" vol. 61, p. 10580 c (1964).

*Primary Examiner*—Norman Morgenstern
*Attorney, Agent, or Firm*—Cushman, Darby & Cushman

[57] ABSTRACT

The present invention relates to the production of the crotoner of cyclohexanone and to its conversion to orthophenylphenol.

12 Claims, No Drawings

PRODUCTION OF ORTHO-PHENYLPHENOL FROM CYCLOHEXANONE

This application is a continuation-in-part of our application Ser. No. 805,028 filed Mar. 6, 1969 now abandoned, and entitled "Ketone Condensation Products".

Orthophenylphenol (O.P.P.) is a chemical which finds its main outlets as a fungicide and dye carrier. Traditionally the commercial source of OPP has been as a by-product of the chlorbenzene route to phenol but as the latter process has been gradually superseded by the cumene route, in which OPP is not a by-product, the supply of OPP has gradually dried up. There being no other commercial route to OPP known, it appeared that this useful chemical would gradually pass out of use.

We have now surprisingly found that cyclohexanone may be converted in a two-stage process to ortho-phenylphenol. Accordingly, the present invention is a process for the production of orthophenylphenol which comprises reacting in a first stage at a temperature in the range 50° to 250°C and in the liquid phase, cyclohexanone with a catalytic amount of a metal compound in which the metal is selected from the group consisting of titanium, vanadium, chromium, manganese, iron, cobalt, nickel, copper, zinc, zirconium, molybdenum, cadmium, tin and tungsten and the compound is selected from the group consisting of a metal salt of a hydrocarbon aliphatic carboxylic acid, the metal salt of naphthenic acid, a metal alkoxide, a polyacid of the metal, heteropolyacid of the metal, the acetylacetonate complex of the metal, and an organic complex of the metal with ethylenediamine tetra-acetic acid, and, in a second stage, dehydrogenating the 2-(1-cyclohexenyl) cyclohexanone so produced to orthophenylphenol.

By a "catalytic amount" we mean that an amount of metal compound is present which is very small in comparison to the amount of ketone present, the metal compound exercising a catalytic effect and not forming part of the product of the reaction. Suitably the amount of metal compound is up to 0.5 mole metal/mole of ketone present, preferably up to 0.05 mole metal/mole of ketone present e.g.: in the range $10^{-5}$ to $10^{-2}$ mole metal/mole of ketone present. When vanadium compounds are used somewhat greater amounts may be used, for example up to 1 mole vanadium/mole of ketone present but it is still preferred that the amount of vanadium used does not exceed 0.5 mole vanadium/mole of ketone present.

More than one metal compound may be used in the first stage of the process, i.e. the conversion of cyclohexanone to 2-(1-cyclohexenyl) cyclohexanone, e.g.: mixtures of vanadium and titanium compounds may be used, and also mixtures of compounds of the same metal.

Organic compounds of the metals are particularly suitable for use in the first stage of the process, preferably metal salts of organic acids, particularly aliphatic carboxylic acids containing up to 20 carbon atoms. Preferred acids are aliphatic carboxylic acids containing between 10 and 20 carbon atoms e.g. vanadium stearate, titanium palmitate, vanadium cleate, and the naphthenic acids e.g.: vanadium naphthenate although we have found that adequate conversions and yields are achieved using salts of carboxylic acids containing fewer than 10 carbon atoms, for example salts of valeric acid, caproic acid, heptanoic acid and nonanoic acid. When a metal carboxylate is used it is advantageous to incorporate the corresponding carboxylic acid into the reaction medium e.g.: stearic acid may be added when vanadium stearate is the catalyst. Preferably the concentration of the carboxylic acid is up to 5% w/w based on the weight of the reaction mixture. Organic complexes of the metals may also be used, for example complexes formed with 1:3-diketones, for example acetylacetone and substituted acetylacetones, and with ethylenediamine tetraacetic acid. Metal alkoxides are also suitable, particularly alkoxides derived from the lower alkanols e.g. alkanols containing up to 6 carbon atoms, for example tetraisopropyltitanate.

Polyacids, for example tungstic acid and the vanadic acids, and heteropoly acids, for example phosphomolybdic acid, silicotungstic acid and phosphovanadic acid may be used as the metal compounds in the first stage of the process.

The first stage of the process is operated in the liquid phase using soluble metal compounds and if necessary increased pressure may be used, at least sufficient to maintain the reaction medium in the liquid phase at the operating temperature. Heterogeneous liquid phase operation is also possible.

The first stage of the process is operated at a temperature in the range 50° to 250°C. preferably in the range 120° to 180°C. A suitable temperature is at or near the boiling point of cyclohexanone.

The reaction is preferably carried out using the ketone as solvent, but if an inert solvent is used it is desirable to maintain a high concentration of ketone in the reaction zone. It is also desirable that water formed during this reaction should be removed, so far as is possible, as soon as it is formed since accumulation of water in the reaction mixture reduces the rate of reaction. The removal of the water formed is conveniently achieved, where possible, by distilling an azeotrope of the ketone and water from the reaction zone. Cyclohexanone forms an azeotrope with water but if necessary an inert azeotroping agent, for example toluene, may be added to the reaction mixture to assist the removal of water. An inert gas purge may also be used to aid water removal.

Preferably oxygen is excluded from the reaction zone and the first stage of the process is operated in an inert atmosphere such as nitrogen or argon to prevent oxidation of the ketone.

The process may be operated batchwise but is preferably continuous. It is particularly advantageous feature of using a catalytic amount of the metal compound that the crotoner product of the first stage of the process, which is obtained in high yield, may be readily separated from the reaction medium for example by distillation, and the catalyst recycled.

Cyclohexanone is obtained commercially by the oxidation of cyclohexane with molecular oxygen frequently in the presence of catalysts such as transition metal or boron compounds. The product of this oxidation is a mixture of cyclohexanol and cyclohexanone but as cyclohexanol is substantially inert to the conditions of the process of the present invention it need not be separated from the cyclohexanone and cyclohexanol/cyclohexanone mixture may be used as feedstock for the present process.

A further form of the invention, therefore, is a process for the production of orthophenylphenol which comprises contacting a mixture of cyclohexanol and cyclohexanone with a catalytic amount of a compound of titanium, vanadium, chromium, manganese, iron, cobalt, nickel, copper, zinc, zirconium, molybdenum, cadmium, tin, or tungsten, separating the 2-(1-cyclohexenyl)cyclohexanone so formed from the cyclohexanol and dehydrogenating the 2-(1-cyclohexenyl) cyclohexanone to orthophenylphenol.

In the first stage of the process of the invention it is preferred to use a catalytic amount of a vanadium compound, preferably vanadium naphthenate as catalyst.

The 2-(1-cyclohexenyl)cyclohexanone may be separated from the cyclohexanol in the above form of the process by distillation.

The second stage of the process of the invention i.e. dehydrogenation of the 2-(1-cyclohexenyl)cyclohexanone to orthophenylphenol may be carried out over any convenient dehydrogenation catalyst. Suitable catalysts are, for example, a noble metal supported on an inert support, for example platinum supported on charcoal, silica or alumina; catalysts containing combinations of metals on inert supports for example nickel and tin supported on silica; and chromia. The supported catalysts suitably comprise 0.5 to 10%, preferably about 5%, of the metal on the support.

The catalysts are used in amounts in the range of 0.5 to 10% is also weight, preferably an amount in the range 4 to 6% by weight. The second stage of the process of the invention is conveniently operated at a temperature in the range of 250° to 500°C and at a pressure in the range 1 to 30 atmospheres. It is preferred to operate the second stage at a combination of temperature and pressure such that the reaction is carried out in the liquid phase, although vapour phase operation isalso possible.

The following examples illustrate the process of the invention.

EXAMPLES 1 TO 8

These examples illustrate the crotonisation of cyclohexanone using catalytic amounts of various metal stearates. The results are shown in Table 1.

In each case, 50 g. cyclohexanone was heated at 155°C. and atmospheric pressure for 190 minutes in the absence of air with $1.4 \times 10^{-3}$ moles of metal added as the metal stearate. Water formed in the reaction was removed continuously by azeotropic distillation with cyclohexanone. The cyclohexanone thus removed was returned to the reaction mixture and the mixture analysed by gas-liquid chromatography. The product 2-(1-cyclohexenyl) cyclohenanone was purified by fractional distillation. The results are shown in Table 1 in which the ketone conversion and yield of 2-(1-cyclohexenyl)cyclohexanone are expressed as mole percentages of the cyclohexanone reacted.

TABLE 1

| Example No. | Metal used (as stearate) | Ketone Conversion % | Yield of 2-(1-cyclohexenyl) cyclohexanone % |
|---|---|---|---|
| 1 | Vanadium | 11 | 94 |
| 2 | Manganese | 11 | 94 |
| 3 | Cobalt | 11 | 90 |
| 4 | Zirconium | 8 | 82 |
| 5 | Zinc | 9 | 75 |
| 6 | Cadmium | 11 | 70 |
| 7 | Tin | 9 | 81 |
| 8 | Titanium | 34 | 92 |

EXAMPLE 9

50 g. cyclohexanone containing $1.4 \times 10^{-3}$ moles of vanadium as vanadium stearate was heated to reflux in the absence of air and at atmospheric pressure. Water was removed continuously from the reaction mixture by azeotropic distillation with cyclohexanone. The reaction temperature was allowed to rise as the concentration of 2-(1-cyclohexenyl)cyclohexanone in the reaction medium increased. After 190 minutes the temperature was 168°C., the cyclohexanone conversion was 40% and the yield of 2-(1-cyclohexenyl)cyclohexanone was 94%. After a further 120 minutes the temperature had risen to 193°C. and the ketone conversion and yield of product were now 71% and 89% respectively.

EXAMPLES 10 TO 12

These examples illustrate the crotonisation of cyclohexanone using various catalytic amounts of vanadium naphthenate. The results are shown in Table 2.

In each case, 50 g. cyclohexanone was heated at 155°C and atmospheric pressure for 190 minutes in the absence of air. Water formed in the reaction was removed continuously by azeotropic distillation with cyclohexanone. The cyclohexanone thus removed was returned to the reaction mixture and the mixture analysed by gas-liquid chromatography.

The results are shown in Table 2 in which the ketone conversion and yield of 2-(1-cyclohexenyl)cyclohexanone are expressed as mole percentages of the cyclohexanone reacted.

TABLE 2

| Example No. | Moles of vanadium naphthenate added | Ketone Conversion % | Yield of 2-(1-cyclohexenyl) cyclohexanone % |
|---|---|---|---|
| 10 | $5.2 \times 10^{-4}$ | 8 | 87 |
| 11 | $1.55 \times 10^{-3}$ | 22 | 90 |
| 12 | $4.75 \times 10^{-3}$ | 56 | 95 |

EXAMPLES 13 TO 15

In each of the following examples, 50 g. cyclohexanone was heated at 155°C. for 190 minutes at atmospheric pressure in the presence of the catalyst. Water formed in the reaction was removed continuously by azeotropic distillation with cyclohexanone. The cyclohexanone thus removed was returned to the reaction mixture. The reaction product was analysed by gas-liquid chromatography. The product 2-(1-cyclohexenyl)-cyclohexanone was purified by fractional distillation. Results are shown in the following Table; the molar yield of 2-(1-cyclohexenyl)cyclohexanone is based on cyclohexanone reacted.

TABLE 3

| Example No. | Catalyst | Moles of catalyst per 50 g. Cyclohexanone (as metal) | Ketone conversion % | Molar Yield of 2-(1-cyclohexenyl) cyclohexanone % |
|---|---|---|---|---|
| 13 | McNAP | $14.5 \times 10^{-4}$ | 11 | 58 |
| 14 | P.M.A. | $15.5 \times 10^{-4}$ | 28 | 77 |
| 15 | S.W.A. | $16.1 \times 10^{-4}$ | 70 | 51 | where
McNAP is molybdenum naphthenate.

P.M.A. is phosphomolybdic acid.
S.W.A. is silicotungstic acid.

EXAMPLES 16 TO 20

These examples illustrate the crotonisation of cyclohexanone using catalytic amounts of various metal carboxylates. The results are shown in Table 4.

In each case, 50 g. (0.51 moles) of cyclohexanone was heated at 155°C and atmospheric pressure for 4 hours in the absence of air with $1.4 \times 10^{-3}$ moles of metal added as the metal carboxylate. Water formed in the reaction was removed continuously by azeotropic distillation with cyclohexanone. The cyclohexanone thus removed was returned to the reaction mixture. The mixture was analysed by infra-red analysis and by nuclear magnetic resonance measurements. The results are shown in Table 4 as molar percentages of 2-(1-cyclohexenyl) cyclohexanone present in the reaction mixture. Neither method is wholly accurate and there is, therefore some discrepancy in the results obtained using the two methods of analysis.

TABLE 4

| Example No. | Metal compound used | molar % 2-(1-cyclohexenyl) cyclohexanone by | |
|---|---|---|---|
| | | I.R. | N.M.R. |
| 16 | Cobalt valerate | 35 | 21 |
| 17 | Cobalt caproate | 50 | 26 |
| 18 | Vanadyl benzoate | 2.5 | 4 |
| 19 | Cobalt heptanoate | 11 | 12 |
| 20 | Cobalt nonanoate | 29 | 24 |

EXAMPLE 21

2-(1-cyclohexenyl)cyclohexanone, produced by the method described in Example 1 was dehydrogenated at 270°C in a hydrogen atmosphere and using 5% weight of a 5% by weight platinum on charcoal catalyst. Substantially all the 2-(1-cyclohexenyl) cyclohexanone reacted under these conditions and the yield of orthophenylphenol was of the order of 85%.

I claim:

1. In a process for the production of orthophenylphenol which comprises reacting, in a first stage, cyclohexanone to produce 2-(1-cyclohexenyl) cyclohexanone, separating the 2-(1-cyclohexenyl) cyclohexanone produced thereby, and, in a second stage, dehydrogenating the separated 2-(1-cyclohexenyl) cyclohexanone so produced to orthophenylphenol;
    the improvement in which, in the first stage, the cyclohexanone is reacted at a temperature in the range of 50° to 250°C in the liquid phase with a catalytic amount of a metal compound in which the metal is selected from the group consisting of titanium, vanadium, chromium, manganese, iron, cobalt, nickel, copper, zinc, zirconium, molybdenum, cadmium, tin and tungsten and the compound is selected from the group consisting of a metal salt of a hydrocarbon aliphatic carboxylic acid, the metal salt of naphthenic acid, a metal alkoxide, a polyacid of the metal, heteropolyacid of the metal, the acetylacetonate complex of the metal, and an organic complex of the metal with ethylenediamine tetra-acetic acid.

2. A process according to claim 1 in which the cyclohexanone is used in admixture with cyclohexanol.

3. A process according to claim 1 in which the amount of metal compound is up to 0.5 mole metal/mole ketone present.

4. A process according to claim 1 in which the metal compound is the metal salt of a hydrocarbon aliphatic carboxylic acid and in which the carboxylic acid corresponding to the metal salt is incorporated in the reaction medium.

5. A process according to claim 1 which comprises contacting cyclohexanone with a metal compound in which the metal is selected from the group consisting of vanadium, cobalt, manganese, titanium and zinc, and in which the compound is selected from the group consisting of a metal salt of a hydrocarbon aliphatic carboxylic acid and the metal salt of naphthenic acid.

6. A process according to claim 1 in which the conversion of cyclohexanone to 2-(1-cyclohexenyl)cyclohexanone is carried out at a pressure sufficient to maintain the reaction medium in the liquid phase at the operating temperature.

7. A process according to claim 1 in which water formed in the conversion of cyclohexanone to 2-(1-cyclohexenyl)cyclohexanone is removed as an azeotrope with the cyclohexanone.

8. A process according to claim 1 in which the conversion of cyclohexanone to 2-(1-cyclohexenyl)cyclohexanone is continuous and the catalyst is recycled.

9. A process according to claim 1 in which the 2-(1-cyclohexenyl) cyclohexanone is dehydrogenated over a catalyst selected from the group consisting of a noble metal supported on an inert support, a combination of metals supported on an inert support, and chromia.

10. A process according to claim 1 in which the 2-(1-cyclohexenyl) cyclohexanone is dehydrogenated over a catalyst selected from the group consisting of platinum supported on charcoal, silica, or alumina and a combination of nickel and tin supported on silica.

11. A process according to claim 1 in which cyclohexanone is contacted at a temperature in the range 50° to 250°C. with an amount of a hydrocarbon aliphatic carboxylate or naphthenate of a metal selected from the group consisting of vanadium, cobalt, manganese and titanium such that the amount of the metal is in the range $10^{-5}$ to $10^{-2}$ mole metal/mole of cyclohexanone to form 2-(1-cyclohexenyl) cyclohexanone, and dehydrogenating the 2-(1-cyclohexenyl)cyclohexanone under dehydrogenation conditions over a dehydrogenation catalyst to form orthophenylphenol.

12. In a process for the production of orthophenylphenol which comprises dehydrogenating 2-(1-cyclohexenyl) cyclohexanone to orthophenylphenol, the 2-(1-cyclohexenyl) cyclohexanone having been obtained by reacting cyclohexanone to produce 2-(1-cyclohexenyl) cyclohexanone, and separating the 2-(1-cyclohexenyl) cyclohexanone produced thereby,
    the improvement in which the cyclohexanone is reacted to produce said 2-(1-cyclohexenyl) cyclohexanone at a temperature in the range of 50° to 250°C in the liquid phase with a catalytic amount of a metal compound in which the metal is selected from the group consisting of titanium, vanadium, chromium, manganese, iron, cobalt, nickel, copper, zinc, zirconium, molybdenum, cadmium, tin and tungsten and the compound is selected from the group consisting of a metal salt of a hydrocarbon aliphatic carboxylic acid, the metal salt of naphthenic acid, a metal alkoxide, a polyacid of the metal, heteropolyacid of the metal, the acetylacetonate complex of the metal, and an organic complex of the metal with ethylenediamine tetra-acetic acid.

* * * * *